US009014924B2

(12) United States Patent
Edara et al.

(10) Patent No.: US 9,014,924 B2
(45) Date of Patent: Apr. 21, 2015

(54) SYSTEM AND METHOD FOR ESTIMATING MATERIAL CHARACTERISTICS

(71) Applicant: Caterpillar Inc., Peoria, IL (US)

(72) Inventors: Thandava K. Edara, Peoria, IL (US); Michael Taylor, Swissvale, PA (US); Timothy Felty, East Peoria, IL (US); Mo Wei, Dunlap, IL (US); Kenneth L. Stratton, Dunlap, IL (US); Troy K. Becicka, Sahuarita, AZ (US)

(73) Assignee: Caterpillar Inc., Peoria, IL (US)

( * ) Notice: Subject to any disclaimer, the term of this patent is extended or adjusted under 35 U.S.C. 154(b) by 203 days.

(21) Appl. No.: 13/722,322

(22) Filed: Dec. 20, 2012

(65) Prior Publication Data
US 2014/0180547 A1 Jun. 26, 2014

(51) Int. Cl.
| G06F 17/00 | (2006.01) |
| G06F 19/00 | (2011.01) |
| E02F 3/76 | (2006.01) |
| G01C 21/30 | (2006.01) |
| G01N 33/00 | (2006.01) |
| G05D 1/02 | (2006.01) |
| E02F 9/20 | (2006.01) |
| E02F 9/26 | (2006.01) |

(52) U.S. Cl.
CPC .............. *G01N 33/00* (2013.01); *G05D 1/0274* (2013.01); *G05D 1/0278* (2013.01); *G05D 2201/0202* (2013.01); *E02F 9/2045* (2013.01); *E02F 9/205* (2013.01); *E02F 9/2054* (2013.01); *E02F 9/262* (2013.01)

(58) Field of Classification Search
USPC .......... 701/48, 49, 50, 400, 409, 300; 74/1 R; 37/381, 382; 172/2, 4.5
See application file for complete search history.

(56) References Cited

U.S. PATENT DOCUMENTS

| 4,926,948 | A | 5/1990 | Davidson et al. |
| 5,462,122 | A | 10/1995 | Yamamoto et al. |
| 5,875,854 | A | 3/1999 | Yamamoto et al. |
| 5,984,018 | A | 11/1999 | Yamamoto et al. |
| 6,076,030 | A | 6/2000 | Rowe |
| 6,181,999 | B1 | 1/2001 | Yamamoto et al. |
| 6,223,110 | B1 | 4/2001 | Rowe et al. |
| 6,421,627 | B1 | 7/2002 | Ericsson |
| 6,655,465 | B2 | 12/2003 | Carlson et al. |
| 6,845,311 | B1 | 1/2005 | Stratton et al. |
| 7,676,967 | B2 | 3/2010 | Gharsalli et al. |
| 8,031,629 | B2 | 10/2011 | Stegmaier et al. |
| 2002/0162668 | A1 | 11/2002 | Carlson et al. |
| 2004/0168358 | A1 | 9/2004 | Stump |
| 2007/0044980 | A1 | 3/2007 | Stratton et al. |
| 2010/0299031 | A1 | 11/2010 | Zhdanov et al. |

FOREIGN PATENT DOCUMENTS

WO WO 2008/118027 A2 10/2008

*Primary Examiner* — Thomas Tarcza
*Assistant Examiner* — Edward Pipala
(74) *Attorney, Agent, or Firm* — Leydig, Voit & Mayer, Ltd.

(57) ABSTRACT

A system for determining material characteristics of a material of a work surface includes a position sensor and a controller. The controller stores a first estimate of the material characteristics and utilizes a planning system to determine an expected profile. The expected profile is based at least in part upon the first estimate of the material characteristics. The controller determines an actual profile of the work surface, compares the expected profile to the actual profile, and determines a second estimate of the material characteristics based at least in part upon the difference between the expected profile and the actual profile.

20 Claims, 6 Drawing Sheets

SYSTEM AND METHOD FOR ESTIMATING MATERIAL CHARACTERISTICS

TECHNICAL FIELD

This disclosure relates generally to controlling a machine and, more particularly, to a system and method for automated estimation of material characteristics of the material upon which the machine is operating.

BACKGROUND

Machines such as dozers, motor graders, wheel loaders, etc., are used to perform a variety of tasks. For example, these machines may be used to move material and/or alter work surfaces at a work site. The machines may operate in an autonomous or semi-autonomous manner to perform these tasks in response to commands generated as part of a work plan for the machines. The machines may receive instructions in accordance with the work plan to perform operations such as digging, loosening, carrying, etc., different materials at the worksite.

Autonomously operated machines may remain consistently productive without regard to a human operator or environmental conditions. In addition, autonomous systems may permit operation in environments that are unsuitable or undesirable for a human operator. Autonomous or semi-autonomous systems may also compensate for inexperienced human operators as well as inefficiencies associated with repetitive tasks.

The work plans may be created in view of the characteristics of the material to be moved. In some instances, the material characteristics used to create the work plans may be based upon standardized materials or estimates of current material conditions. In other instances, material conditions may be measured in a variety of manners. If the actual characteristics of the material do not match those used for the work plans, the work plans may not be executed in an efficient manner.

U.S. Patent Publication No. 2010/0299031 discloses a system for controlling an earthmoving machine in which resistance force vectors of soil resistance to cutting and dragging may be determined and used as input to the control system. The resistance force vector may depend on the volume, weight and condition of the material in front of the blade.

The foregoing background discussion is intended solely to aid the reader. It is not intended to limit the innovations described herein, nor to limit or expand the prior art discussed. Thus, the foregoing discussion should not be taken to indicate that any particular element of a prior system is unsuitable for use with the innovations described herein, nor is it intended to indicate that any element is essential in implementing the innovations described herein. The implementations and application of the innovations described herein are defined by the appended claims.

SUMMARY

In one aspect, a system for determining material characteristics of a material of a work surface includes a position sensor associated with a machine for generating position signals indicative of a position of the work surface and a controller. The controller is configured to store a first estimate of the material characteristics and to utilize a planning system to determine an expected profile extending along a path. The expected profile is based at least in part upon the first estimate of the material characteristics. The controller is further configured to receive a plurality of position signals from the position sensor as the machine moves along the work surface and a work implement of the machine moves a volume of material along the path, to determine an actual profile of the work surface, to compare the expected profile to the actual profile, and to determine a second estimate of the material characteristics based at least in part upon the difference between the expected profile and the actual profile.

In another aspect, a method for determining material characteristics of a material of a work surface includes storing a first estimate of the material characteristics and utilizing a planning system to determine a expected profile extending along a path. A machine is moved along the work surface with a work implement to modify the work surface. The expected profile is based at least in part upon the first estimate of the material characteristics. The method further includes receiving a plurality of position signals from a position sensor associated with the machine as the machine moves along the work surface, the position signals being indicative of a position of the work surface. The method also includes determining the position of the work surface to define an actual profile of the work surface, comparing the expected profile to the actual profile, and determining a second estimate of the material characteristics based at least in part upon the difference between the expected profile and the actual profile.

In still another aspect, a machine includes a prime mover, a ground engaging work implement for engaging a work surface, and a position sensor for generating position signals indicative of a position of the work surface. A controller is configured to store a first estimate of the material characteristics of the material and to utilize a planning system to determine a expected profile extending along a path. The expected profile is based at least in part upon the first estimate of the material characteristics of the material. The controller is further configured to receive a plurality of position signals from the position sensor as the machine moves along the work surface and a work implement of the machine moves a volume of material along the path, to determine an actual profile of the work surface based upon the position signals, to compare the expected profile to the actual profile, and to determine a second estimate of the material characteristics based at least in part upon the difference between the expected profile and the actual profile.

DETAILED DESCRIPTION

Figure 1:
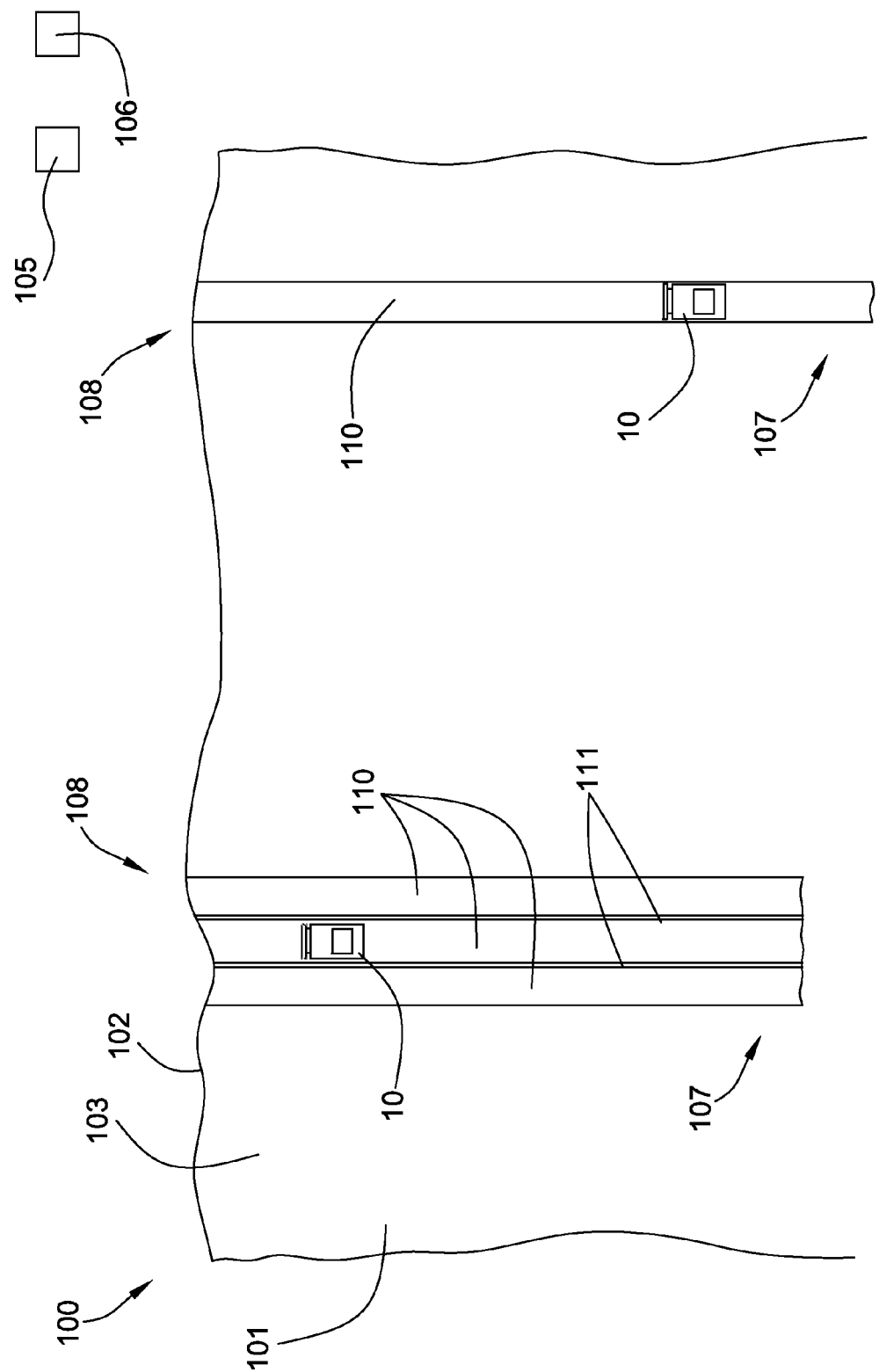
FIG. 1 shows a schematic view of a work site at which a machine incorporating the principles disclosed herein may be used.

FIG. 1 depicts a diagrammatic illustration of a work site 100 at which one or more machines 10 may operate in an autonomous, a semi-autonomous, or manual manner. Work site 100 may be a portion of a mining site, a landfill, a quarry, a construction site, or any other area in which movement of material is desired. Tasks associated with moving material may include a dozing operation, grading operation, a leveling operation, a bulk material removal operation, or any other type of operation that results in alteration of the current topography at work site 100. As depicted, work site 100 includes a work area 101 having a crest 102 defining an edge of a ridge, embankment, high wall or other change in elevation. Work surface 103 may take any form and refers to the actual profile or position of the terrain of the work area.

As used herein, a machine 10 operating in an autonomous manner operates automatically based upon information received from various sensors without the need for human operator input. As an example, a haul truck that automatically follows a path from one location to another and dumps a load at an end point may be operating autonomously. A machine operating semi-autonomously includes an operator, either within the machine or remotely, who performs some tasks or provides some input and other tasks are performed automatically and may be based upon information received from various sensors. As an example, a truck that automatically follows a path from one location to another but relies upon an operator command to dump a load may be operating semi-autonomously. In another example of a semi-autonomous operation, an operator may dump a bucket of an excavator in a load truck and a controller may automatically return the bucket to a position to perform another digging operation. A machine being operated manually is one in which an operator is controlling all or essentially all of the functions of the machine. A machine may be operated remotely by an operator (i.e., remote control) in either a manual or semi-autonomous manner.

Figure 2:
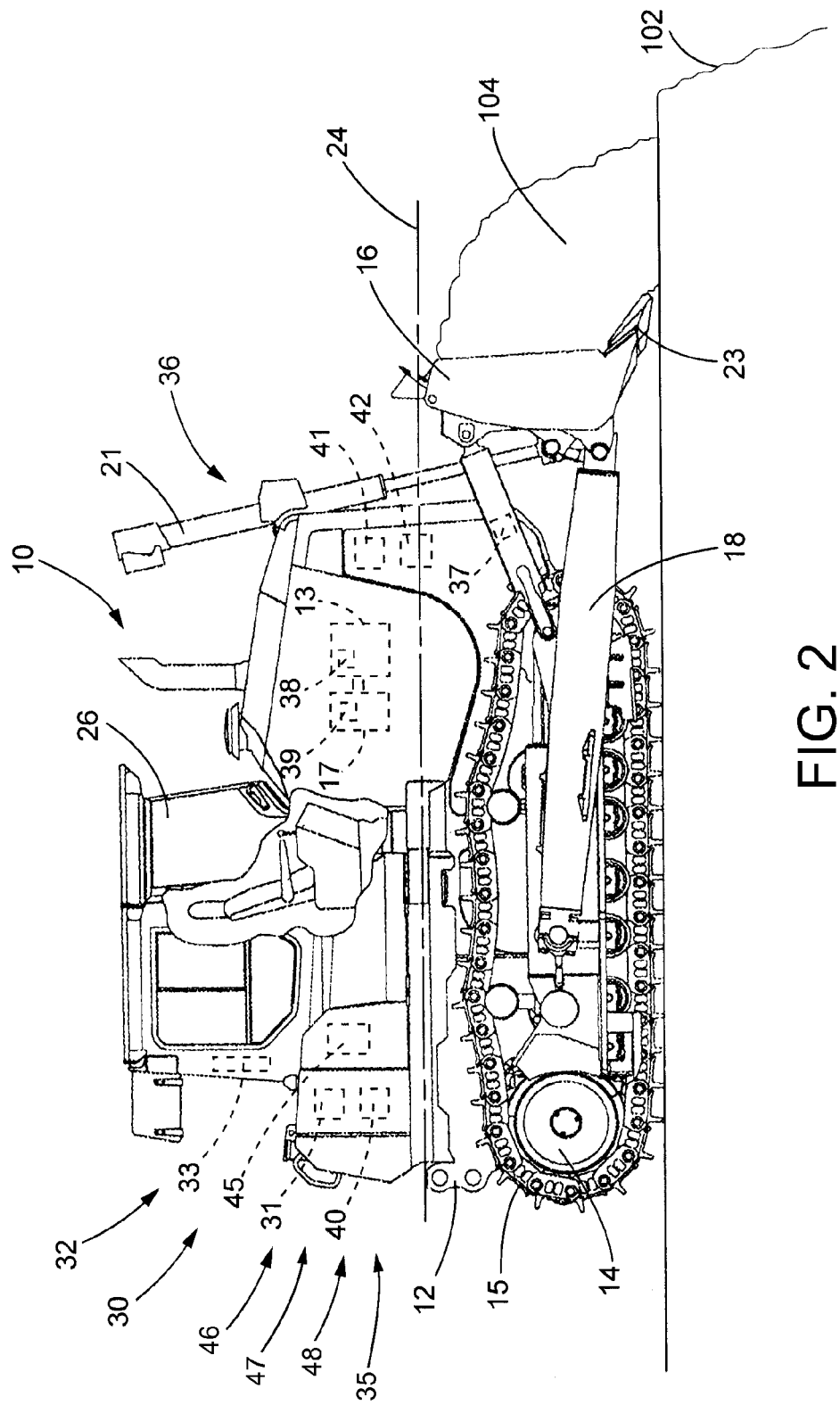
FIG. 2 shows a diagrammatic illustration of a machine in accordance with the disclosure.

FIG. 2 shows a diagrammatic illustration of a machine 10 such as a dozer adjacent crest 102 with a work implement or a blade 16 pushing material 104 over the crest. The machine 10 includes a frame 12 and a prime mover such as an engine 13. A ground-engaging drive mechanism such as a track 15 is driven by a drive wheel 14 on each side of machine 10 to propel the machine 10. Although machine 10 is shown in a "track-type" configuration, other configurations, such as a wheeled configuration, may be used. Operation of the engine 13 and a transmission (not shown) which are operatively connected to the drive wheels 14 and tracks 15 may be controlled by a control system 30 including a controller 31. Other types of prime movers and drive systems are contemplated.

Machine 10 may include a ground engaging work implement such as blade 16 pivotally connected to frame 12 by arms 18 on each side of machine 10. First hydraulic cylinder 21 coupled to frame 12 supports blade 16 in the vertical direction, and allows blade 16 to move up or down vertically from the point of view of FIG. 2. Second hydraulic cylinders 22 on each side of machine 10 allow the pitch angle of blade tip 23 to change relative to a centerline 24 of the machine.

Machine 10 may be equipped with a plurality of sensors that provide data indicative (directly or indirectly) of various operating parameters of the machine. A hydraulic system may include sensors for monitoring pressure within the system as well as the pressure of specific cylinders. For example, one or both of the second hydraulic cylinders 22 may include an associated pressure sensor 37. Sensors may be provided to monitor the operating conditions of the engine 13 and the associated drivetrain such as an engine speed sensor 38 and a torque converter speed sensor 39. The machine may also include an accelerometer 40 for determining the acceleration of the machine along various axes. Still further, a pitch angle sensor 41 and a pitch rate sensor 42 may be included for determining roll, pitch and yaw of machine 10. Other sensors necessary or desirable for operating the machine 10 may be provided.

Machine 10 may be controlled by a control system 30 that interacts with a positioning system such as a global positioning system ("GPS") to monitor and/or control the movement of the machine about the work site 100. The control system 30 may be located on the machine 10 and/or may be located at a command center 105 (FIG. 1) located remotely from the machine. In certain embodiments, the functionality of control system 30 may be distributed so that certain functions are performed at machine 10 and other functions are performed at command center 105. For example, a network system such as wireless network system 106 (FIG. 1) may provide generalized commands or information to the machine 10 that the portions of control system 30 on the machine utilize to generate specific commands to operate the various systems of machine 10. In the alternative, aspects of the control system 30 remote from the machine 10 may provide some or all of the specific commands that are then transmitted by the wireless network system 106 to systems of the machine. Machine 10 may be one of several machines operating at work site 100, each of which may communicate with the wireless network system 106.

Rather than operating the machine 10 in an autonomous manner, an operator may have the ability to operate the machine 10 remotely such as with a wireless control unit 45. Still further, machine 10 may also include a cab 26 that an operator may physically occupy and provide input to control the machine. Cab 26 may include one or more input devices through which the operator issues commands to control the propulsion and steering of the machine as well as operate various implements associated with the machine. In one embodiment, machine 10 may be configured to be operated autonomously, semi-autonomously, or manually. In case of semi-autonomous or manual operation, the machine may be operated by remote control and/or by an operator physically located within the cab 26.

The control system 30, as shown generally by an arrow in FIG. 2 indicating association with the machine 10, may include an electronic control module or controller 31. The controller 31 may receive input command signals from the wireless network system 106, remote control input command signals from an operator operating machine 10 remotely, or operator input command signals from an operator operating the machine 10 from within cab 26. The controller 31 may control the operation of the drivetrain as well as the hydraulic systems that operate the ground engaging work implement such as blade 16. The control system 30 may include one or more sensors to provide data and other input signals representative of various operating parameters of the machine 10. The term "sensor" is meant to be used in its broadest sense to include one or more sensors and related components that may be associated with the machine 10 and that may cooperate to sense various functions, operations, and operating characteristics of the machine.

The controller 31 may be an electronic controller that operates in a logical fashion to perform operations, execute control algorithms, store and retrieve data and other desired operations. The controller 31 may include or access memory, secondary storage devices, processors, and any other components for running an application. The memory and secondary storage devices may be in the form of read-only memory (ROM) or random access memory (RAM) or integrated circuitry that is accessible by the controller. Various other circuits may be associated with the controller such as power supply circuitry, signal conditioning circuitry, driver circuitry, and other types of circuitry.

The controller 31 may be a single controller or may include more than one controller disposed to control various functions and/or features of the machine 10. The term "controller" is meant to be used in its broadest sense to include one or more controllers and/or microprocessors that may be associated with the machine 10 and that may cooperate in controlling various functions and operations of the machine. The functionality of the controller 31 may be implemented in hardware and/or software without regard to the functionality. The controller 31 may rely on one or more data maps relating to the operating conditions of the machine 10 that may be stored in the memory of controller. Each of these data maps may include a collection of data in the form of tables, graphs, and/or equations.

A position sensing system 32, as shown generally by an arrow in FIG. 2 indicating association with the machine 10, may include a position sensor 33 to sense a position of the machine relative to the work area 101. The position sensor 33 may include a plurality of individual sensors that cooperate to provide signals to controller 31 to indicate the position of the machine 10. The controller 31 may determine the position of the machine 10 within work area 101 as well as the orientation of the machine such as its heading, pitch and roll. In doing so, the dimensions of the machine 10 may be stored within the controller 31 with the position sensing system defining a datum or reference point on the machine and the controller using the dimensions to determine the position of the terrain or work surface 103 upon which the machine is moving. Such position sensor 33 may be a series of GPS sensors, an odometer or other wheel rotation sensing sensor, a perception based system or may use other systems such as lasers to determine the position of machine 10.

Machine 10 may be configured to move material at the work site 100 according to one or more material movement plans from an initial location 107 to a spread or dump location 108. The dump location 108 may be at crest 102 or at any other location. The material movement plans may include, among other things, forming a plurality of spaced apart channels or slots 110 that are cut into the work surface at work site 100 along a path from the initial location 107 to the dump location 108. In doing so, each machine 10 may move back and forth along a linear path between the initial location 107 and the dump location 108. If desired, a relatively small amount of material may be left or built up as walls 111 between adjacent slots 110 to prevent or reduce spillage and increase the efficiency of the material moving process. The walls 111 between the slots 110 may be moved after the slots are formed or periodically as desired. The process of moving material through slots 110 while utilizing walls 111 of material to increase the efficiency of the process is sometime referred to as "slot dozing."

Figure 3:
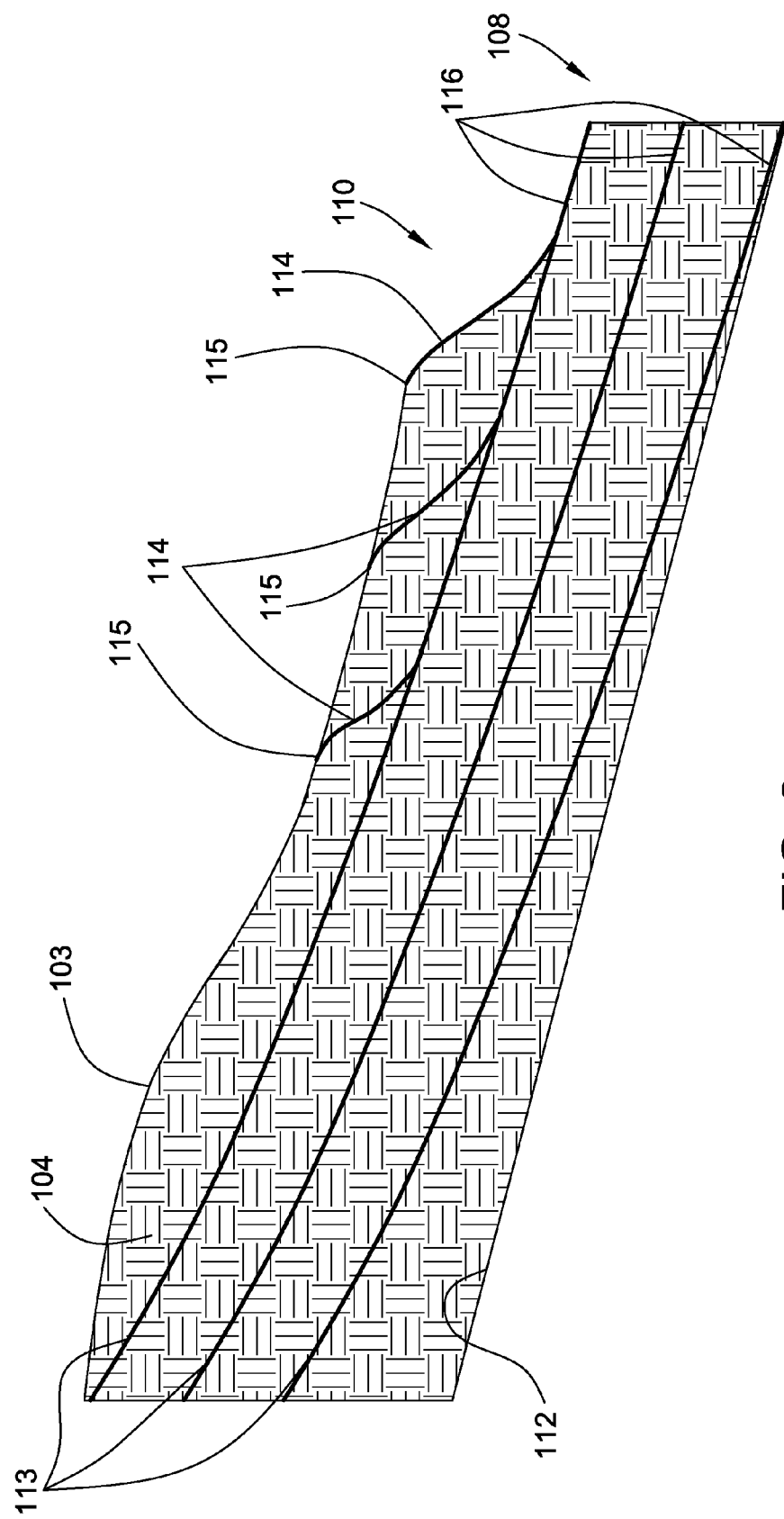
FIG. 3 shows a cross-section of a portion of a work site depicting various aspects of a material moving plan.

As depicted in FIG. 3, in one embodiment, each slot 110 may be formed by initially setting the desired parameters of the final work surface or final design plane 112. Material may be removed from the work surface 103 in one or more layers or passes 113 until the final design plane 112 is reached. The blade 16 of machine 10 may engage the work surface 103 with a series of cuts 114 that are spaced apart lengthwise along the slot 110. Each cut 114 begins at a cut location 115 along the work surface 103 at which the blade 16 initially engages the work surface and extends into the material 104 towards the pass target or carry surface 116 for a particular pass. Controller 31 may be configured to guide the blade 16 along each cut 114 until reaching the carry surface 116 and then follow the carry surface towards the dump location 108.

Figure 4:
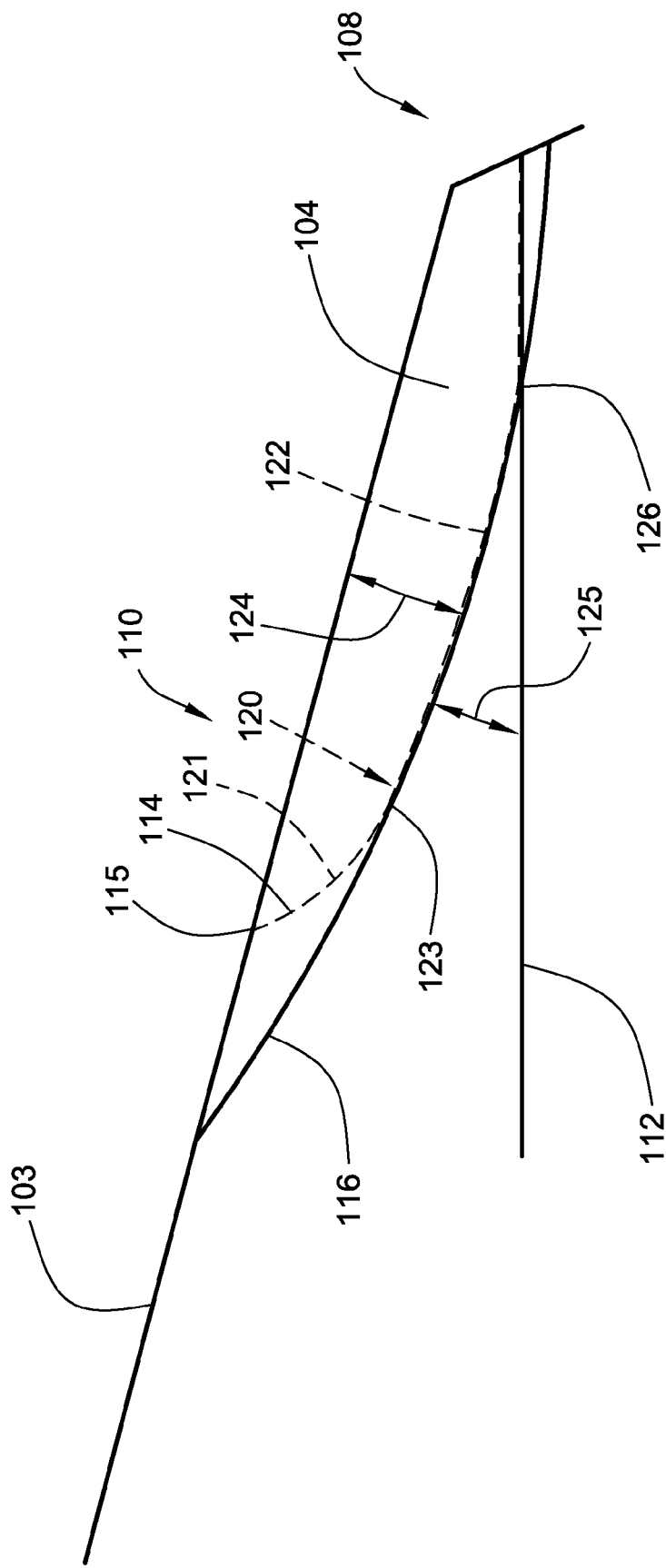
FIG. 4 shows a diagrammatic cross-section of a portion of a work site depicting a potential expected profile.

During each material moving pass, the controller 31 may be configured to guide the blade 16 generally along a desired path such as a target or expected profile depicted by dashed line 120 in FIG. 4 from the cut location 115 to the dump location 108. A first portion 121 of the expected profile 120 extends from the cut location 115 to the carry surface 116. The first portion 121 may be referred to as the loading profile as that is the portion of the expected profile 120 at which the blade 16 is loaded with material. A second portion 122 of the expected profile 120 extends from the intersection 123 of the cut 114 and the carry surface 116 to the dump location 108. The second portion 122 may be referred to as the carry profile as that is the portion of the expected profile 120 at which the blade 16 carries the load along the carry surface 116.

The first portion 121 or loading profile may have any configuration and, depending on various factors including the configuration of the work surface 103 and the type of material to be moved, some cut profiles may be more efficient than others. The loading profile may be formed of one or more segments that are equal or unequal in length and with each having different or identical shapes. These shapes may be linear, symmetrically or asymmetrically curved, Gaussian-shaped or any other desired shape. In addition, the angle of any of the shapes relative to the work surface 103 or the final design plane 112 may change from segment to segment.

The second portion 122 or carry profile may have any configuration but is often generally linear and sloped downward so that movement of material will be assisted by gravity to increase the efficiency of the material moving process. In other words, the carry profile is often configured so that it slopes downward towards the dump location 108. The carry profile (sometimes referred to as the slot parameters) may define the shape of the carry surface 116, the depth of the carry surface 116 below an uppermost surface of the work surface 103 as indicated by reference number 124, and the angle of the carry surface as indicated by reference number 125. In some instances, the angle 125 of the carry surface may be defined relative to a gravity reference or relative to the final design plane 112.

Although it may be generally desirable for the blade 16 to follow the expected profile 120, performance characteristics of the machine 10 and/or desired operating efficiencies may cause a deviation from the expected profile 120. More specifically, as blade 16 makes a cut 114, the load on the blade will increase. Further, as the blade 16 travels along the carry surface 116, the load on the blade will likely continue to increase. If the blade 16 is overloaded for a particular slope, the machine 10 may slip and/or cause excess wear on the machine. Accordingly, the control system 30 may include a blade control system 46 to maximize the efficiency of the material moving process.

In one embodiment, the blade control system 46 may control the load on the blade 16 so that the torque generated by the machine 10 is generally maintained at or about a predetermined value. In one example, it may be desirable to maintain the load on the machine 10 at approximately 80% of its maximum torque. In other examples, it may be desirable to maintain the load at a range of approximately 70-90% of the maximum torque. Other values and ranges are contemplated. In order to maintain the load at a desired value or within a desired range, the blade control system 46 may raise or lower the blade 16 to decrease or increase the amount of material carried by the blade 16 and thus decrease or increase the load. It should be noted that since the work surface 103 may be at different angles relative to a gravity reference, the load on the blade 16 corresponding to a particular load (e.g. 80% of the maximum machine load) will likely vary depending on the slope at which the machine 10 is operating.

The control system 30 may include an implement load monitoring system 35 shown generally by an arrow in FIG. 2. The implement load monitoring system 35 may include a variety of different types of implement load sensors depicted generally by an arrow in FIG. 2 as an implement load sensor system 36 to measure the load on the blade 16. In one embodiment, the implement load sensor system 36 may embody one or more pressure sensors 37 for use with one or more hydraulic cylinder, such as second hydraulic cylinders 22, associated with blade 16. Signals from the pressure sensor 37 indicative of the pressure within the second hydraulic cylinders 22 may be monitored by controller 31. The load on the blade 16 may be correlated to the load on the engine 13 by controller 31. Other manners of determining a change in cylinder pressure associated with a change in the load on blade 16 are contemplated, including other manners of measuring the pressure within second hydraulic cylinders 22 and measuring the pressure within other cylinders associated with the blade.

The load on the blade 16 may be affected by the slope of the terrain upon which the machine 10 is moving. Accordingly, if desired, the accuracy of the implement load measurement may be increased by utilizing the implement load sensor system 36 in conjunction with a slope or inclination sensor such as pitch angle sensor 41. For example, if the machine 10 is moving uphill, the load on the blade 16 may be higher due to gravity as compared to a machine operating in the same conditions on flat terrain. Similarly, the load on the blade 16 may be lower for the same conditions when operating the machine in a downhill orientation. By determining the slope of the terrain, the controller 31 may more accurately determine changes in the load on the blade 16.

If desired, a machine load monitoring system 47 may be included in control system 30. The machine load monitoring system 47 may utilize the engine speed sensor 38 and the torque converter speed sensor 39 to measure a difference between the speed of the engine 13 and the torque converter 17 to determine the load on the machine 10.

Control system 30 may also include a module or planning system 48 for determining or planning various aspects of the excavation plan. The planning system 48 may receive various types of input such as the configuration of the work surface 103, the final design plane 112, the cut location 115, a desired loading profile, a desired carry profile, and characteristics of the material to be moved. Operating characteristics and capabilities of the machine 10 such as maximum load may also be entered into the planning system 48. The planning system 48 may simulate the results of cutting at a particular cut location and for a particular expected profile, and then choose a cut location that creates the most desirable results based on one or more criteria.

In one example, the planning system 48 may calculate a volume of material that will be moved by the blade 16 as it travels along a first expected profile corresponding to a first cut location 115. Based on the calculated volume of material that will be moved, the planning system 48 may modify the cut location 115 to define a second expected profile. The planning system 48 may then calculate a volume of material to be moved based upon the second expected profile. This process may be iteratively repeated until the planning system 48 selects an acceptable cut location that meets some predetermined criteria. After the planning system 48 selects an acceptable cut location 115, the cut location and its corresponding expected profile may be utilized to guide the machine and the blade 16 and move material along the path to the dump location 108.

In one embodiment, the planning system 48 may be part of the controller 31 and perform while operating the machine 10. In another embodiment, the calculations may be performed ahead of time and the various inputs to the planning system 48 and the resultant cut locations 115 and expected profiles 120 stored as part of the data maps of the controller 31. In such case, upon setting the desired inputs and determining the configuration of the work surface 103, an acceptable cut location 115 and corresponding expected profile 120 may be determined by the controller 31 through the use of its data maps.

FIG. 4 is an illustration of a potential cut 114 at work site 100 that may be generated by control system 30. Work surface 103 represents the uppermost height of the existing material at the slot 110. While the illustration is depicted in two dimensions, it should be appreciated that the data representing the illustration may be in three dimensions. For example, the data representing work surface 103 may include a plurality of data points that represent the uppermost height of existing material at a plurality of locations along work surface 103. This information may be obtained according to any method known in the art. In one example, the machine 10 may utilize the position sensing system 32 described above to map out the contour of work surface 103 as machine 12 moves across it. This data may also be obtained according to other methods such as by a vehicle that includes lasers and/or cameras. It should be noted that as the machine 10 moves material to the dump location 108, the position of the work surface 103 may be updated based upon the current position of the machine 10 and the position of the blade 16.

The loading profile begins at cut location 115 on work surface 103 and ends at carry surface 116. As depicted in FIG. 4, the loading profile may be generally arcuate with a generally symmetrical curve. The carry surface 116 may be generally arcuate and curved downward to utilize gravity in an advantageous manner. It should be noted that the carry surface 116 is depicted as passing below the final design plane 112. In such case, the controller 31 may be configured to guide the blade 16 so that it does not pass below the final design plane 112. In other words, the expected profile 120 defined by the planning system 48 may direct the blade 16 to move along the cut 114 while loading the blade, to move along the carry surface 116 beginning at the intersection 123 of the cut 114 and the carry surface 116 until reaching the intersection 126 of the carry surface 116 and the final design plane 112 and then move along the final design plane until reaching the dump location 108. This path is depicted by a dashed line in FIG. 4.

As may be seen in FIG. 4, moving the blade 16 along the expected profile 120 will result in a volume of material 104 being moved from slot 110. The planning system 48 may use the shape of the loading profile and the cut location 115 to determine the volume of material that would be moved by blade 16 if the machine 10 were to follow the expected profile 120. More specifically, the planning system 48 may use three-dimensional data that is used to represent the machine 10, the work surface 103, and the expected profile 120 to make a volumetric calculation of the volume of material that will be moved for a particular expected profile 120.

As stated above, the planning system 48 may be configured to utilize as an input the expected characteristics of the material being moved by machine 10. For example, an operator or some other personnel may input into control system 30 an estimate of the type or characteristics of the material that will be moved or a default value may be set within the controller 31. However, in some instances, the actual material characteristics may not match the expected material characteristics.

If the material characteristics (such as density, liquid content, or viscosity) are different from those that which were expected, the planning system 48 may define the expected profile 120 in a manner that is difficult for the blade 16 to follow. As a result, the blade control system 46 may cause the blade 16 to deviate from the expected profile 120 which may reduce the efficiency of the material moving process.

Figure 5:
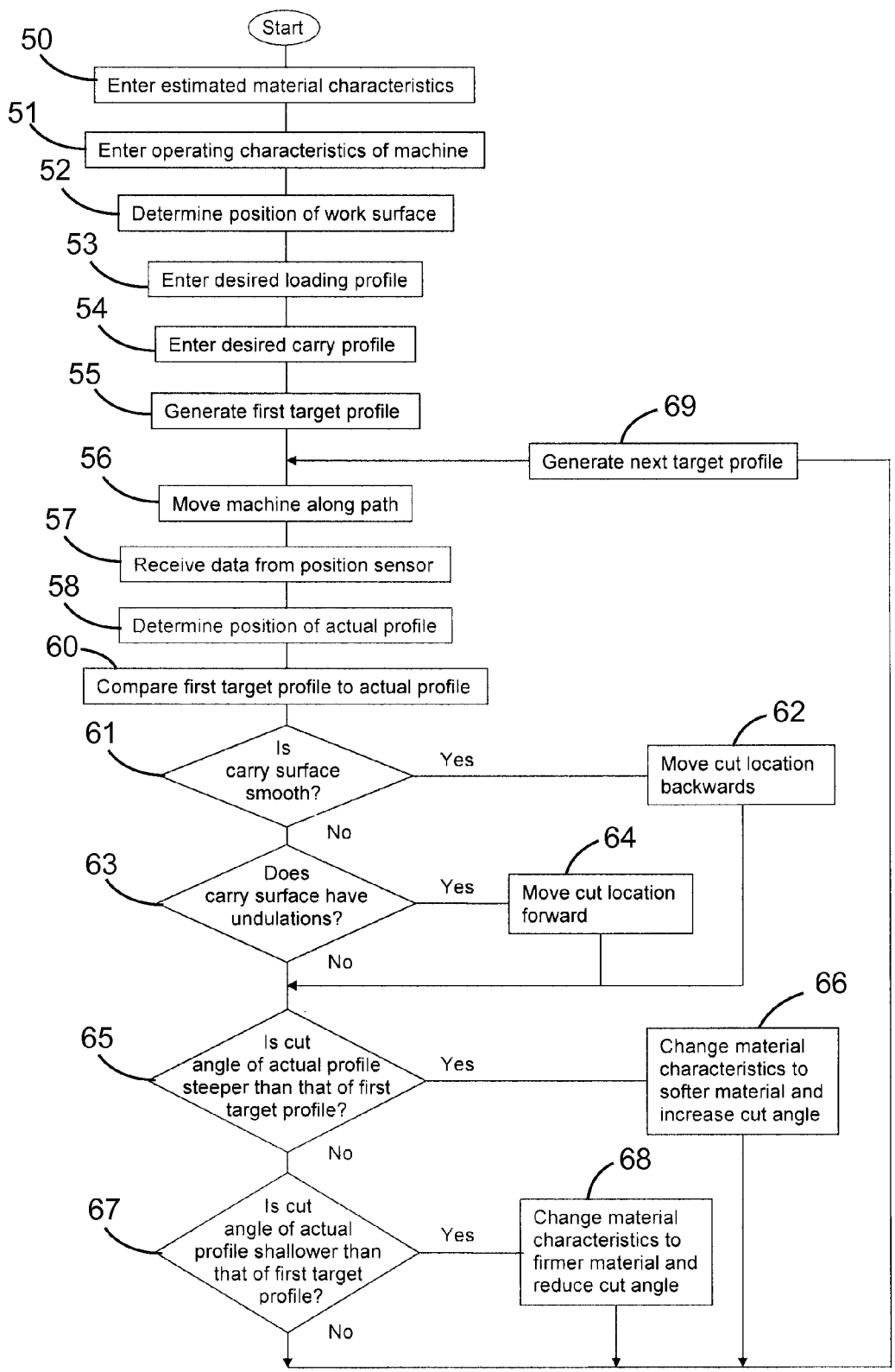
FIG. 5 shows a flowchart illustrating a material characteristic estimation process in accordance with the disclosure.

FIG. 5 depicts a process for automatically modifying the material characteristics within the controller 31. The automatic modification of the material characteristics may then result in modifications to the planning system 48 of the control system 30. More specifically, at stage 50, characteristics of the material to be moved may be entered into controller 31. These characteristics may include, for example, the density, liquid content, and/or viscosity of the material. In some instances, it may be possible to enter weather conditions into the controller 31.

At stage 51, the operating characteristics of the machine 10 may be entered into controller 31. These characteristics may include a desired maximum load on the machine 10 that may be used by the blade control system 46. Various dimensions of the machine 10 may also be entered into controller 31 such as the dimensions of the blade 16, which may be used by controller 31 to determine the volume of material moved by the machine 10.

At stage 52, the position or configuration of the work surface 103 may be determined. The configuration of the work surface 103 may be determined by the topographical map of the earth at the work area 101. In an alternate step, the configuration of the work surface 103 may be determined by moving a mapping vehicle along the work surface to establish its configuration. In still another alternate step, the machine 10 may be moved along the work surface 103 and the position sensor 33 may provide a plurality of signals to controller 31 to indicate the position of the machine 10. The controller 31 may determine the position of the machine 10 within the work area 101 as well as the orientation of the machine such as its heading, pitch and roll. Based upon the known dimensions of the machine 10 stored within the controller 31 and the position sensing system 32 defining a data or reference point on the machine, the controller 31 may determine the configuration of the work surface 103 over which the machine 10 is traveling.

At stage 53, the desired first portion 121 of the expected profile 120 or loading profile may be entered into controller 31. As stated above, the loading profile may have any configuration. If desired, the loading profile may be broken into a series of segments that may be equal or unequal in length and each segment may have a different shapes or identical shapes. The angle of each of the segments may vary from segment to segment if desired.

At stage 54, the carry profile or slot parameters may be entered into controller 31. The carry profile may define the shape of the carry surface 116, the depth of the carry surface 116 below an uppermost surface 124 of the work surface 103, and the angle 125 of the carry surface 116 relative to a fixed reference. In FIG. 4, the angle 125 is relative to the final design plane 112.

At stage 55, a cut location 115 may be set or determined and entered into controller 31. The controller 31 may utilize at stage 56 the cut location 115, the estimated material characteristics entered at stage 50, the operating characteristics of the machine 10 entered at stage 51, the configuration of the work surface 103 determined at stage 52, the desired loading profile entered at stage 53, and the desired carry profile entered as stage 54 to determine a expected profile 120. The controller 31 may use an iterative process as described above with respect to the planning system 48 to determine the expected profile 120. A expected profile 120 is depicted relative to work surface 103 in FIG. 6.

At stage 56, the machine 10 is moved along the path from the initial location 107 to the dump location 108. As the machine moves along the path, the controller 31 may receive at stage 57 data from the position sensor 33.

Inasmuch as the position sensor 33 may not be positioned immediately adjacent the work surface 103, the controller 31 may utilize the known dimensions of the machine 10 together with the data from the position sensor 33 to determine at stage 58 the configuration of the actual profile or work surface 103. Other manners of determining the configuration of the actual profile are contemplated.

At stage 60, the controller 31 compares the expected profile 120 to the actual profile or work surface 103 measured during or after the machine 10 has moved from the initial location 107 to the dump location 108. With this comparison, the controller 31 may determine a modified estimate of the material characteristics of the material.

Figure 6:
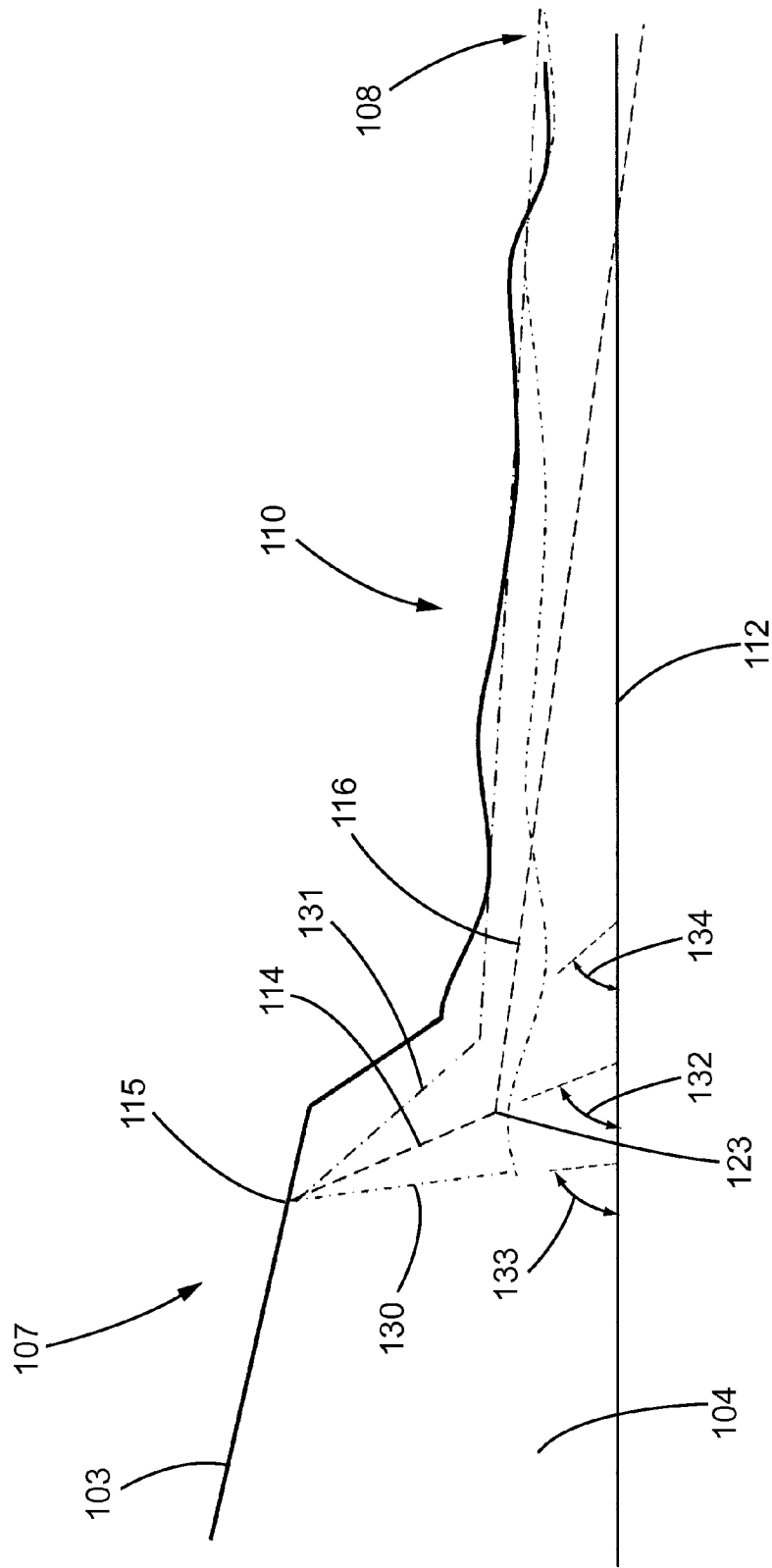
FIG. 6 shows a diagrammatic cross section of a slot depicting alternate paths of a work implement depending upon the characteristics of the material being moved.

More specifically, if the material 104 being moved is softer than that which is expected or estimated, the blade 16 will tend to dig into the material faster than expected and thus the actual profile will not match the expected profile 120. In addition, by digging into the material 104 faster than expected, the blade 16 will likely be loaded faster than expected. Accordingly, the actual profile will not match the expected profile 120 and therefore the blade control system 46 may raise the blade 16 above the carry surface 116 to reduce the load thereon. Accordingly, the blade 16 may only minimally contact the carry surface 116 and thus may not remove undulations from the carry surface. A profile of blade movement with material softer than expected is depicted in FIG. 6 by reference number 130.

If the material 104 is harder or firmer than expected, the blade 16 may not cut into the work surface 103 in as steep an angle as that of the expected profile and therefore the blade may be under-loaded once it reaches the carry surface 116. Under-loading the blade 16 may reduce the operating efficiency of the machine 10. A profile of blade movement with material firmer than expected is depicted in FIG. 6 by reference number 131.

Referring back to FIG. 5, after comparing the expected profile 120 to the actual profile at stage 60, the controller 31 may, at decision stage 61, determine whether the carry surface 116 is relatively smooth. If the carry surface is relatively smooth, the controller 31 may be configured to automatically move, at stage 62, the cut location 115 backwards or away from the dump location 108 and towards the initial location 107. Moving the cut location 115 backwards will increase the amount of material engaged by blade 16.

If the carry surface 116 is not relatively smooth at decision stage 61, the controller 31 may determine whether the carry surface has relatively large undulations at decision stage 63. If the carry surface 116 has relatively large undulations, the controller 31 may determine that the blade control system 46 is moving the blade 16 upward as it moves along the carry surface 116 and thus is not sufficiently engaging the carry surface to remove the undulations. This may be due to the blade 16 having too large of a load once it reaches the carry surface 116. In such case, the controller 31 may be configured to move, at stage 64, the cut location forward or towards the dump location 108 and away from the initial location 107.

At decision stage 65, the controller 31 may determine whether the cut angle of the actual profile is steeper than that of the expected profile. More specifically, referring to FIG. 6, it may be seen that the cut angle 133 of the profile 130 is steeper relative to the final design plane 112 than the cut angle 132 of expected profile 120. In such case, the controller 31 may, at stage 66, change the material characteristics within the controller to reflect a softer, less dense or lighter material. In addition, if desired, the planning system 48 may also increase the cut angle 132 when planning subsequent cuts.

If the cut angle 132 of the actual profile is not steeper than that of the first expected profile at decision stage 65, the controller 31 may determine at decision stage 67 whether the cut angle 132 of the actual profile is shallower than that of the expected profile 120. Referring to FIG. 6, the cut angle 134 of the profile 131 relative to the final design stage 111 is shallower than the cut angle 132 of the expected profile 120. In such case, the controller 31 may automatically change the estimate of the material characteristics so as to reflect a firmer, more dense, or heavier material. In addition, the controller 31 may cause the planning system 48 to reduce the cut angle 132 when planning subsequent cuts.

After the material characteristics have been evaluated and modified at stage 66 or 68 or left unmodified because the cut angle of the actual profile matches that of the expected profile, the controller 31 may calculate the next expected profile at stage 69 and the process of evaluating the material characteristics may be repeated.

INDUSTRIAL APPLICABILITY

The industrial applicability of the control system 30 described herein will be readily appreciated from the forgoing discussion. The foregoing discussion is applicable to machines 10 that utilize or rely upon the characteristics of the material on which they operate as part of the input to operation of the machines. For example, machine 10 may include a system that utilizes the characteristics of the material being moved to plan the material movement operation. Such systems may be used at a mining site, a landfill, a quarry, a construction site, or any other area in which movement of material is desired.

As the machine 10 moves, the controller 31 may monitor various systems and operating conditions of the machine. The controller 31 may compare a expected profile 120 along which the blade 16 was intended to move to an actual profile along which the blade actually moved. By comparing the expected profile 120 to the actual profile, the controller 31 may determine whether the material being moved is firmer or softer than that which was expected or had been previously utilized in the planning system 48. The controller 31 may modify the characteristics of the material utilized by the planning system 48 to alter the operation of the planning system 48. By increasing the accuracy of the material characteristics used by planning system 48, the operation of the machine 10 may be increased. The controller 31 may also use the modified material characteristics for other systems if desired.

It will be appreciated that the foregoing description provides examples of the disclosed system and technique. All references to the disclosure or examples thereof are intended to reference the particular example being discussed at that point and are not intended to imply any limitation as to the scope of the disclosure more generally. For example, although described in the context of slot dozing, the foregoing description is applicable to a wide variety of environments, operations, and applications. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A system for determining material characteristics of a material of a work surface, comprising:
    a position sensor associated with a machine for generating position signals indicative of a position of the work surface; and
    a controller configured to:
        store a first estimate of the material characteristics;
        utilize a planning system to determine an expected profile extending along a path, the expected profile based at least in part upon the first estimate of the material characteristics;
        receive a plurality of position signals from the position sensor as the machine moves along the work surface and a work implement of the machine moves a volume of material along the path;
        determine an actual profile of the work surface based at least in part upon the position signals;
        compare the expected profile to the actual profile; and
        determine a second estimate of the material characteristics based at least in part upon a difference between the expected profile and the actual profile.

2. The system of claim 1, wherein the controller is further configured to modify the planning system based at least in part upon the second estimate of the material characteristics.

3. The system of claim 1, wherein the position sensor is on the machine and the controller is further configured to receive the plurality of position signals as the machine moves along the path.

4. The system of claim 3, wherein the position sensor generates position signals indicative of a position of the machine and the controller is further configured to determine the actual profile based at least in part upon the position of the machine.

5. The system of claim 1, wherein the difference between the expected profile and the actual profile defines a cut angle, and the second estimate of the material characteristics reflects softer conditions of the material if the cut angle is steeper than the expected profile.

6. The system of claim 1, wherein the difference between the expected profile and the actual profile defines a cut angle, and the second estimate of the material characteristics reflects firmer conditions of the material if the cut angle is shallower than the expected profile.

7. The system of claim 1, wherein the controller is further configured to adjust an angle of at least a portion of a subsequent expected profile relative to the work surface based at least in part on the second estimate of the material characteristics.

8. The system of claim 1, wherein at least a portion of the expected profile is at an angle to the work surface.

9. The system of claim 1, wherein the path includes a dump location, and the controller is further configured to move a cut location of the work implement relative to the dump location when determining subsequent expected profiles based at least in part upon the difference between the expected profile and the actual profile.

10. The system of claim 1, wherein the expected profile has a first section generally at a first angle to the work surface and a second section generally at a second angle to the work surface, and wherein the first angle is greater than the second angle.

11. The system of claim 10, wherein the path includes a dump location, and the controller is further configured to move a cut location of the work implement relative to the dump location when determining subsequent expected profiles based at least in part upon the difference between the second section of the expected profile and a second section of the actual profile corresponding along the path to the second section of the expected profile.

12. The system of claim 11, wherein the controller is configured to move the cut location of the work implement towards the dump location if the second section of the actual profile has undulations larger than a predetermined size.

13. The system of claim 12, wherein the controller is configured to move the cut location of the work implement away from the dump location if the second section of the actual profile has undulations no larger than a predetermined size.

14. The system of claim 1, wherein the planning system is configured to operate at least in part based upon the first estimate of the material characteristics and operation of the planning system is automatically modified based upon a difference between the expected profile and the actual profile.

15. A controller implemented method for determining material characteristics of a material of a work surface, comprising:
   storing a first estimate of the material characteristics;
   utilizing a planning system to determine an expected profile extending along a path, the expected profile based at least in part upon the first estimate of the material characteristics;
   moving a machine along the work surface with a work implement to modify the work surface;
   receiving a plurality of position signals from a position sensor associated with the machine as the machine moves along the work surface, the position signals being indicative of a position of the work surface;
   determining an actual profile of the work surface based upon the position signals;
   comparing the expected profile to the actual profile; and
   determining a second estimate of the material characteristics based at least in part upon the difference between the expected profile and the actual profile.

16. The method of claim 15, further including modifying the planning system based at least in part upon the second estimate of the material characteristics.

17. The method of claim 15, further including defining a cut angle based upon a difference between the expected profile and the actual profile, and the second estimate of the material characteristics reflects softer conditions of the material if the cut angle is steeper than the expected profile.

18. The method of claim 15, further including defining a cut angle based upon a difference between the expected profile and the actual profile, and the second estimate of the material characteristics reflects firmer conditions of the material if the cut angle is shallower than the expected profile.

19. The method of claim 15, further including adjusting an angle of at least a portion of a subsequent target profile relative to the work surface based at least in part on the second estimate of the material characteristics of the material.

20. A machine comprising:
   a prime mover;
   a ground engaging work implement for engaging a work surface;
   a position sensor for generating position signals indicative of a position of the work surface; and
   a controller configured to:
      store a first estimate of material characteristics of a material of the work surface;
      utilize a planning system to determine an expected profile extending along a path, the expected profile based at least in part upon the first estimate of the material characteristics;
      receive a plurality of position signals from the position sensor as the machine moves along the work surface and a work implement of the machine moves a volume of material along the path;
      determine an actual profile of the work surface based upon the position signals;
      compare the expected profile to the actual profile; and
      determine a second estimate of the material characteristics based at least in part upon the difference between the expected profile and the actual profile.

* * * * *